US012121378B2

(12) United States Patent
Sheng et al.

(10) Patent No.: US 12,121,378 B2
(45) Date of Patent: Oct. 22, 2024

(54) SYSTEMS AND METHODS FOR IMAGE-GUIDED RADIOTHERAPY USING DUAL ROBOT ARCHITECTURE

(71) Applicant: The Regents of the University of California, Oakland, CA (US)

(72) Inventors: Ke Sheng, Los Angeles, CA (US); Salime M. Boucher, Santa Monica, CA (US)

(73) Assignees: The Regents of the University of California, Oakland, CA (US); Radiabeam Technologies, LLC, Santa Monica, CA (US)

( * ) Notice: Subject to any disclaimer, the term of this patent is extended or adjusted under 35 U.S.C. 154(b) by 1066 days.

(21) Appl. No.: 16/487,946

(22) PCT Filed: Feb. 23, 2018

(86) PCT No.: PCT/US2018/019541
§ 371 (c)(1),
(2) Date: Aug. 22, 2019

(87) PCT Pub. No.: WO2018/156968
PCT Pub. Date: Aug. 30, 2018

(65) Prior Publication Data
US 2019/0380666 A1 Dec. 19, 2019

Related U.S. Application Data

(60) Provisional application No. 62/463,388, filed on Feb. 24, 2017.

(51) Int. Cl.
*A61B 6/10* (2006.01)
*A61B 6/03* (2006.01)
(Continued)

(52) U.S. Cl.
CPC .............. *A61B 6/102* (2013.01); *A61B 6/035* (2013.01); *A61B 6/4085* (2013.01);
(Continued)

(58) Field of Classification Search
CPC ........... A61B 6/032; A61B 6/035; A61B 6/08; A61B 6/4085; A61B 6/4441;
(Continued)

(56) References Cited

U.S. PATENT DOCUMENTS

| 5,207,223 A | 5/1993 | Adler |
| D646,703 S | 10/2011 | Wong |

(Continued)

FOREIGN PATENT DOCUMENTS

| CN | 101217913 A | 7/2008 |
| CN | 103099630 A | 3/2015 |

(Continued)

OTHER PUBLICATIONS

International Searching Authority, International Search Report and Written Opinion for application PCT/US2018/019541, mailed on May 2, 2018, 6 pages.

(Continued)

*Primary Examiner* — Keith M Raymond
*Assistant Examiner* — Milton Truong
(74) *Attorney, Agent, or Firm* — Quarles & Brady LLP

(57) ABSTRACT

A system for coordinating radiation therapy and imaging processes includes a radiation therapy system an radiation source mounted on a robotically-controlled system to move the radiation source about a subject to direct radiation to a target area in the subject according to a treatment plan. The system also includes an imaging system configured to acquire imaging data from a subject. The imaging system and the radiation therapy system are independently movable. The system also includes a coordination system configured (Continued)

to coordinate operation of the imaging system to acquire the imaging data from the subject during movement of the radiation source about the subject according to the treatment plan to avoid collisions of the radiation therapy system with the imaging system.

20 Claims, 6 Drawing Sheets

(51) Int. Cl.
A61B 6/40 (2024.01)
A61N 5/10 (2006.01)

(52) U.S. Cl.
CPC ......... *A61N 5/1038* (2013.01); *A61N 5/1045* (2013.01); *A61N 5/1083* (2013.01); *A61N 2005/1061* (2013.01)

(58) Field of Classification Search
CPC ..... A61B 6/4458; A61B 6/4482; A61B 6/486; A61B 6/102; A61B 34/30; A61N 2005/1061; A61N 5/1038; A61N 5/1045; A61N 5/1049; A61N 5/1064; A61N 5/1067; A61N 5/1083; A61N 5/107
See application file for complete search history.

(56) References Cited

U.S. PATENT DOCUMENTS

| | | | |
|---|---|---|---|
| 2006/0074292 A1 | 4/2006 | Thomson | |
| 2010/0195792 A1 | 8/2010 | Kunz | |
| 2011/0080990 A1* | 4/2011 | Filiberti | G16H 20/40 378/65 |
| 2012/0008734 A1* | 1/2012 | Thomson | A61N 5/1049 378/22 |
| 2012/0008735 A1* | 1/2012 | Maurer | A61B 6/488 378/5 |
| 2012/0035462 A1* | 2/2012 | Maurer, Jr. | A61N 5/1045 600/431 |
| 2014/0163736 A1* | 6/2014 | Azizian | B25J 9/1676 700/259 |
| 2015/0173690 A1 | 6/2015 | Ning et al. | |
| 2015/0190656 A1* | 7/2015 | Kuduvalli | A61N 5/1048 901/44 |
| 2015/0209599 A1* | 7/2015 | Schlosser | A61B 8/085 600/427 |
| 2016/0023019 A1* | 1/2016 | Filiberti | A61N 5/107 600/1 |
| 2016/0183899 A1* | 6/2016 | Vancamberg | A61B 6/4476 378/37 |
| 2018/0056090 A1* | 3/2018 | Jordan | A61N 5/1081 |

FOREIGN PATENT DOCUMENTS

| | | |
|---|---|---|
| WO | 2010030463 A1 | 3/2010 |
| WO | 2011156526 A2 | 12/2011 |
| WO | 2014018983 A1 | 1/2014 |
| WO | 2016140955 | 9/2016 |

OTHER PUBLICATIONS

European Patent Office. Extended European Search Report for application 18756705.2, Mailed on Nov. 11, 2020. 7 pages.

* cited by examiner

SYSTEMS AND METHODS FOR IMAGE-GUIDED RADIOTHERAPY USING DUAL ROBOT ARCHITECTURE

CROSS-REFERENCE TO RELATED APPLICATIONS

This application represents the national stage entry of International Application PCT/US2018/019541, filed on Feb. 23, 2018, which claims benefit of and priority to U.S. Application 62/463,388, filed Feb. 24, 2017, and entitled "SYSTEMS AND METHODS FOR IMAGE-GUIDED RADIOTHERAPY USING DUAL ROBOT ARCHITECTURE.", which is incorporated herein by reference in its entirety for all purposes.

STATEMENT REGARDING FEDERALLY SPONSORED RESEARCH

This invention was made with government support under grant CA183390, awarded by the National Institutes of Health. The government has certain rights in the invention.

BACKGROUND

The present disclosure generally relates to image-guided radiation therapy systems and methods.

Conventional external beam radiation therapy, also referred to as "teletherapy," is commonly administered by directing a linear accelerator ("LINAC") to produce beams of ionizing radiation that irradiates the defined target volume in a subject. The radiation beam is a single beam of radiation that is delivered to the target region from several different directions, or beam paths. Together, the determination of how much dose to deliver along each of these beam paths constitutes the so-called radiation therapy "plan." The purpose of the treatment plan is to accurately identify and localize the target volume in the subject that is to be treated.

Intensity modulated radiation therapy ("IMRT") is an external beam radiation therapy technique that utilizes computer planning software to produce a three-dimensional radiation dose map, specific to a target tumor's shape, location, and motion characteristics. Various regions within a tumor and within the subject's overall anatomy may receive varying radiation dose intensities through IMRT, which treats a subject with multiple rays of radiation, each of which may be independently controlled in intensity and energy. Each of these rays or beams is composed of a number of sub-beams or beamlets, which may vary in their individual intensity, thereby providing the overall intensity modulation. Because of the high level of precision required for IMRT methods, detailed data must be gathered about tumor locations and their motion characteristics. In doing so, the radiation dose imparted to healthy tissue can be reduced while the dose imparted to the affected region, such as a tumor, can be increased. In order to achieve this, accurate geometric precision is required during the treatment planning stage.

Image-guided radiation therapy ("IGRT") employs medical imaging, such as computed tomography ("CT"), concurrently with the delivery of radiation therapy to a subject undergoing treatment. In general, IGRT is employed to accurately direct radiation therapy using positional information from the medical images to supplement a prescribed radiation delivery plan. The advantage of using IGRT is twofold. First, it provides a means for improved accuracy in delivering radiation fields. Second, it provides a method for reducing the dose imparted to healthy tissue during treatment. Moreover, higher accuracy in delivering radiation fields allows for dose escalation in tumors, without appreciably increasing dose levels to the surrounding healthy tissue. Also, dose escalation allows for treatments to be completed in fewer fractions, creating greater throughput and fewer subject visits.

Radiation therapy systems having a LINAC disposed on an articulated arm have been shown to be advantageous platforms for delivering radiation dose that is highly conformal to a tumor while minimizing dose to the surrounding normal tissue. However, to accurately treat the tumor, the tumor's precise location needs to be determined. In some existing radiation therapy systems with image-guidance, X-ray sources, typically mounted on the ceiling of the treatment room, are used to image the subject. Although these sources can provide real time 2D radiographic images for treatment alignment, they cannot be used to generate CT images of the subject. In addition, 2D radiographic images lack volumetric information and cannot image tumors with only soft tissue contrast, which in many cases is highly desired. On the other hand, CT imaging systems are based on C-arm and ring gantry systems to image and set-up the subjects, and are limited in the range of motion and flexibility of treatment.

In light of the above, there is a need for improved systems and methods for image-guided radiation treatment.

SUMMARY

The present disclosure overcomes the aforementioned drawbacks by providing systems and methods for the robotic coordination of external beam radiation therapy and non-fluoroscopic or multi-dimensional imaging.

In accordance with one aspect of the disclosure, a system is provided for coordinating radiation therapy and imaging processes. The system includes a radiation therapy system comprising a radiation source mounted on a robotically-controlled system that is configured to move the radiation source about a subject and direct radiation to a target area in the subject according to a treatment plan. The system also includes an imaging system configured to acquire imaging data from a subject. The imaging system and the radiation therapy system are independently movable. The system further includes a coordination system configured to coordinate operation of the imaging system to acquire the imaging data from the subject during movement of the radiation source about the subject according to the treatment plan to avoid collisions of the radiation therapy system with the imaging system.

In accordance with another aspect of the present disclosure, a method for coordinating radiation therapy and imaging processes is provided. The method includes receiving an instruction for carrying out a radiation therapy process corresponding to a treatment plan, and directing, using a coordination system, a radiation therapy system to initiate the radiation therapy process in which a radiation source mounted on a robotically-controlled system directs radiation to a target area in the subject according to the treatment plan. The method also includes directing, using the coordination system, an imaging system to acquire imaging data from a subject. The imaging system and the radiation therapy system are independently movable. The method further includes coordinating, using the coordination system, operation of the imaging system during movement of the radiation source about the subject to avoid collision of the radiation therapy system with the imaging system.

DETAILED DESCRIPTION

The following systems and methods address one or more of the aforementioned problems and provides additional advantages. As will be described, a flexible image-guided radiation therapy system is provided that utilizes a robotically controlled external beam director and a robotically controlled imaging device controlled in a coordinated fashion. In some aspects, the system allows for real-time control and monitoring of radiation therapy using volumetric images.

Figure 1:
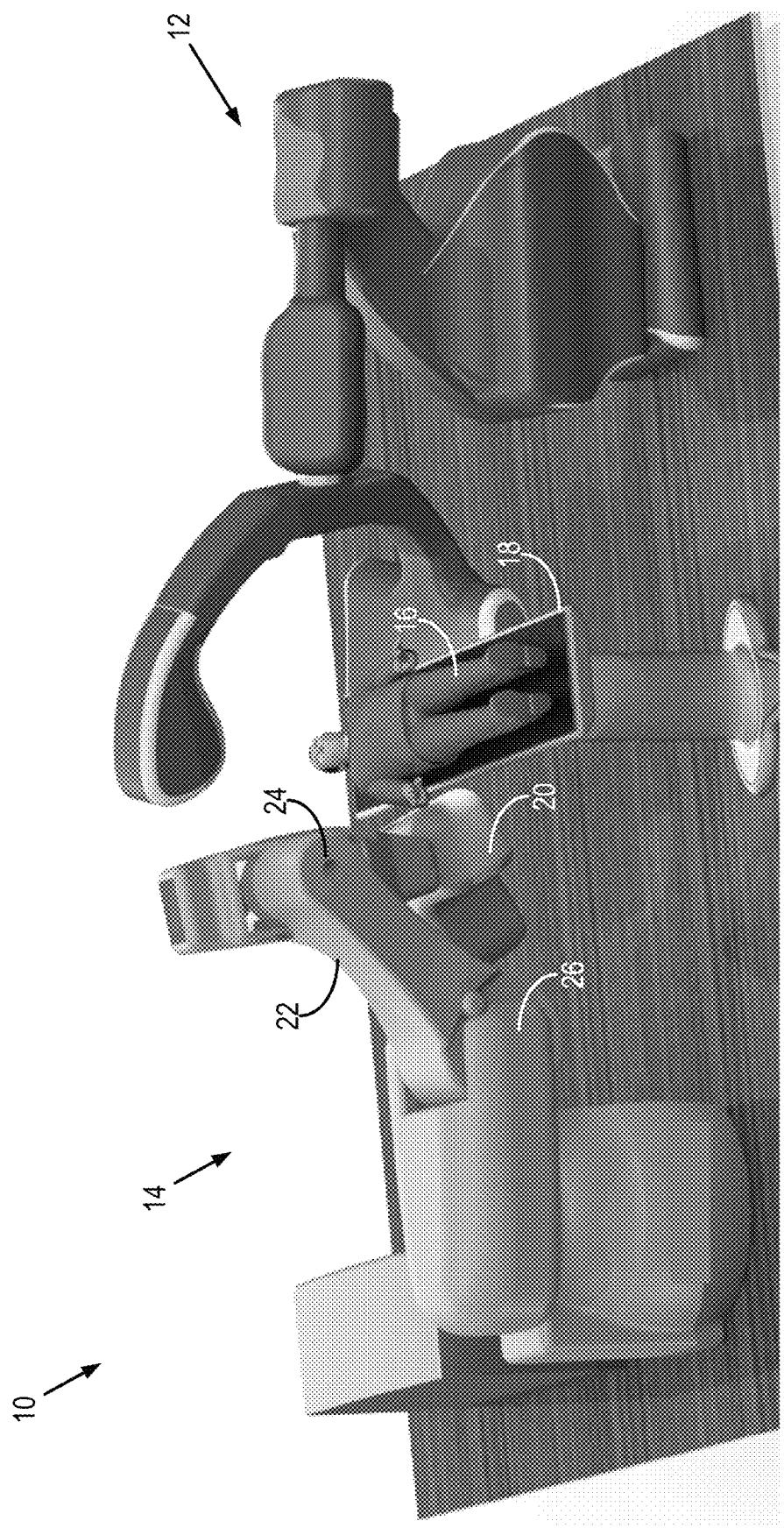
FIG. 1 illustrates an embodiment of the radiation therapy system of the present disclosure having a robotic arm for both the ionizing radiation source and the imaging device.

Referring to FIG. 1, a control-coordinated, image-guided radiation therapy and imaging system 10 according to one non-limiting implementation of the present disclosure is provided. The system 10 includes a robotically-controlled imaging system 12 and a robotically-controlled radiation-therapy (or "radiation therapy") system 14 that, as will be described, are controlled to operate in coordination to form a combined imaging and therapy architecture. Specifically, the imaging system 12 is configured to acquire images of subject or subject 16 lying on subject table 18 and can, as non-limiting example, form a computed tomography (CT) system, including a cone-beam CT system. The radiation therapy system 14 includes a radiation source, such as a linear accelerator (LINAC) that may be partially or entirely located in a head of beam director 20. The radiation source may be configured to generate high-energy x-rays or electrons, as well as other forms of therapeutic radiation.

The radiation therapy system 14 includes an articulated arm 22 that can have, as non-limiting example, at least two joints 24, 26 that allow the beam director 20, and the radiation source 20, to move with at least 4 degrees of freedom, and in some configurations, six degrees of freedom. The imaging system 12 can acquire images of the subject 16, including images of any tumors, and provide feedback of those images to radiation therapy system 14, so that the radiation therapy delivered to subject 16 can be altered in real-time. As will be described, the system 10 includes one or more controllers or coordination systems configured to operate the imaging system 12 and radiation therapy system 14 so that radiation therapy system 14 can receive information from imaging system 12 and so that the respective positioning, imaging, and beam operation of the imaging system 12 and radiation therapy system 14 can be controlled robotically.

The radiation therapy system 14 may be an image-guided radiation therapy ("IGRT") system; however, it should be readily appreciated by those skilled in the art that the invention can additionally be practiced in any number of radiation therapy systems. For example, stereotactic radiosurgery systems such as the CyberKnife® system (Accuray, Sunnyvale, California), traditional gantry-mounted LINAC systems, and cobalt-60 teletherapy systems can be readily employed. Additionally, hadron therapy systems, such as proton beam therapy systems and heavy ion beam therapy systems, may be employed when practicing the invention. It will also be appreciated by those skilled in the art that in addition to therapeutic x-rays, IGRT and intensity modulated radiation therapy ("IMRT") systems may use gamma rays produced, for example, by a cobalt-60 radiation source to deliver therapeutic radiation to a subject.

Figure 2:
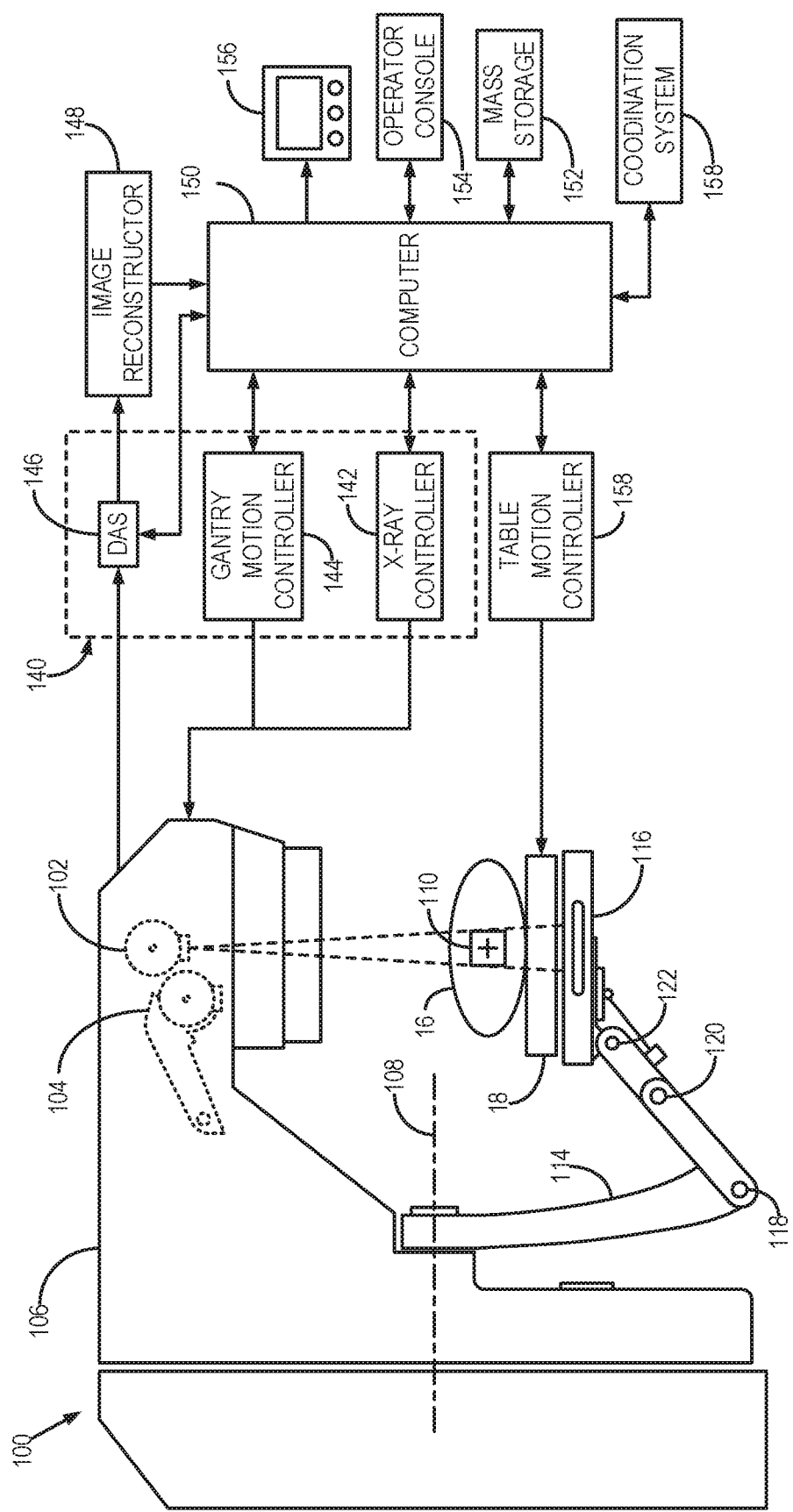
FIG. 2 is a block diagram of an exemplary image-guided radiation therapy ("IGRT") system of FIG. 1.

Referring to FIG. 2, an exemplary image-guided radiation therapy ("IGRT") system 100 includes a therapeutic x-ray source 102. The system may include a diagnostic x-ray source 104, or this diagnostic x-ray source 104 may be foregone in favor of the imaging system 12, as will be described. If included, the diagnostic x-ray source 104 projects a cone-beam of x-rays toward a detector array 116. Both the therapeutic x-ray source 102 and diagnostic x-ray source 104 are attached adjacent each other and housed at the same end of a first rotatable gantry 106, which rotates about a pivot axis 108. The first rotatable gantry 106 allows either of the x-ray sources, 102 and 104, to be aligned in a desired manner with respect to a target area or volume 110 in a subject 16 positioned on a subject table 18. A second rotatable gantry 114 is rotatably attached to the first rotatable gantry 106 such that it too is able to rotate about the pivot axis, 108.

Disposed on one end of the second rotatable gantry 114 is an x-ray detector 116. The x-ray detector 116 can function not only as a diagnostic image device when receiving x-rays from the diagnostic x-ray source 104, but also as a portal image device when receiving x-rays from the therapeutic x-ray source 102. However, the capabilities of the diagnostic x-ray source 104 and the use of the x-ray detector 116 as a diagnostic image device is substantially limited because, for example, it cannot achieve any degrees of freedom apart from the therapeutic x-ray source 102 and is further limited by the simple rotation achieved about the pivot axis 108.

The detector 116 is formed by a number of detector elements that together sense the projected x-rays that pass through the subject 16. Each detector element produces an electrical signal that represents the intensity of an impinging x-ray beam and, hence, the attenuation of the beam as it passes through the subject 16. The second rotatable gantry 114 further includes an articulating end that can pivot about three points 118, 120, and 122. The pivoting motion provided by these points 118, 120, and 122, allows the x-ray detector 116 to be moved within a two-dimensional plane. However, the capabilities of the diagnostic x-ray source 104 and the use of the x-ray detector 116 as a diagnostic image device is substantially limited because to this 2D plane. Thus, as will be described, the present disclosure overcomes this by the above-referenced combination of the imaging system 12 and radiation therapy system 14, in which case when referencing FIG. 2, the IGRT system 100 functions as the radiation therapy system 14 of FIG. 1.

As a further limitation, in a traditional system, the rotation of the rotatable gantries, 106 and 114, and the operation of the x-ray sources, 102 and 104, are governed by a control mechanism 140 of the IGRT system. The control mechanism 140 includes an x-ray controller 142 that provides power and timing signals to the x-ray sources, 102 and 104, and a gantry motor controller 144 that controls the rotational speed and position of the gantries, 106 and 114. A data acquisition system ("DAS") 146 in the control mechanism 140 samples analog data from detector elements and converts the data to digital signals for subsequent processing. An image reconstructor 148, receives sampled and digitized x-ray data from the DAS 146 and performs high speed image reconstruction. The reconstructed image is applied as an input to a computer 150 which stores the image in a mass storage device 152.

The computer 150 also receives commands and scanning parameters from an operator via a console 154 that has a keyboard. An associated display 156 allows the operator to observe the reconstructed image and other data from the computer 150. The operator supplied commands and parameters are used by the computer 150 to provide control signals and information to the DAS 146, the x-ray controller 142 and the gantry motor controller 144. In addition, the computer 150 operates a table motor controller 158 which controls the motorized subject table 18 to position the subject 16 within the gantries, 106 and 114.

As will be further described, the computer 150 is coupled to a coordination system 158. The coordination system 158 provides an overarching communication and control architecture to coordinate operation of the IGRT system 100 with a separate imaging system. That is, as will be described, the coordination system 158 allows the robotically-controlled imaging system 12 and the robotically-controlled radiation therapy system 14 to operate in concert and function and one coordinated system 10.

Figure 3:
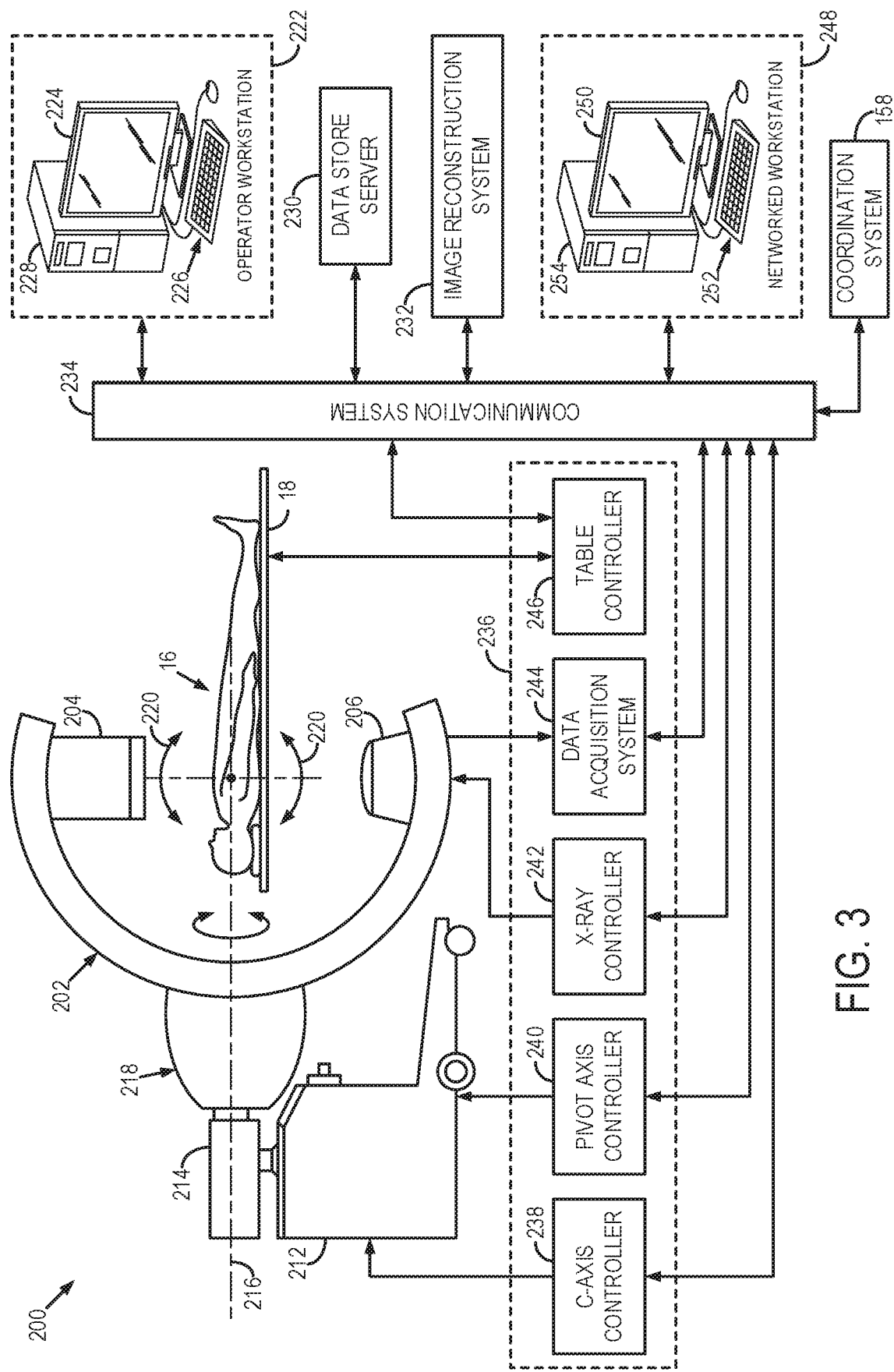
FIG. 3 is a block diagram of a multi-dimensional imaging system, in this case, a computed tomography system, of FIG. 1.

Referring now to FIG. 3, an example of a so-called "C-arm" x-ray imaging system 200 is illustrated. While a C-arm system is shown, other imaging systems and configurations are likewise usable. However, the C-arm imaging system 200 is advantageous use in connection with interventional procedures and similar procedures, other configurations may be utilized, including traditional, gantry or bore-oriented imaging systems. The C-arm x-ray imaging system 200 includes a gantry 202 having a C-arm to which an x-ray source assembly 204 is coupled on one end and an x-ray detector array assembly 206 is coupled at its other end. The gantry 202 enables the x-ray source assembly 204 and detector array assembly 206 to be oriented in different positions and angles around the subject 16, such as a medical subject or an object undergoing examination that is positioned on the subject table 18. Notably, instead of a simple gantry, a robot with a multitude of articulating joints and arms may be utilized, which provides more angles from which acquire images and utilize to avoid collisions. When the subject 16 is a medical subject, this configuration enables a physician and, as will be described, radiation therapy access to the subject 16.

The x-ray source assembly 204 includes at least one x-ray source that projects an x-ray beam, which may be a fan-beam or cone-beam of x-rays, towards the x-ray detector array assembly 206 on the opposite side of the gantry 202. The x-ray detector array assembly 206 includes at least one x-ray detector, which may include a number of x-ray detector elements. Examples of x-ray detectors that may be included in the x-ray detector array assembly 206 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 206 sense the projected x-rays that pass through the subject 16. Each x-ray detector element produces an electrical signal that may represent the intensity of an impinging x-ray beam and, thus, the attenuation of the x-ray beam as it passes through the subject 208. In some configurations, each x-ray detector element is capable of counting the number of x-ray photons that impinge upon the detector. During a scan to acquire x-ray projection data, the gantry 202 and the components mounted thereon rotate about an isocenter of the C-arm x-ray imaging system 200. As will be described, the coordination system 158, facilitates operation of the system 200 along with the above-described radiation therapy system 100 to act in concert.

The gantry 202 includes a support base 212. A support arm 214 is rotatably fastened to the support base 212 for rotation about a horizontal pivot axis 216. The pivot axis 216 is aligned with the centerline of the subject table 18 and the support arm 214 extends radially outward from the pivot axis 216 to support a C-arm drive assembly 218 on its outer end. The C-arm gantry 202 is slidably fastened to the drive assembly 218 and is coupled to a drive motor (not shown) that slides the C-arm gantry 202 to revolve it about a C-axis, as indicated by arrows 220. The pivot axis 216 and C-axis are orthogonal and intersect each other at the isocenter of the C-arm x-ray imaging system 200, which is indicated by the black circle and is located above the subject table 18.

The x-ray source assembly 204 and x-ray detector array assembly 206 extend radially inward to the pivot axis 216 such that the center ray of this x-ray beam passes through the system isocenter. The center ray of the x-ray beam can thus be rotated about the system isocenter around either the pivot axis 216, the C-axis, or both during the acquisition of x-ray attenuation data from a subject 16 placed on the subject table 18. During a scan, the x-ray source and detector array are rotated about the system isocenter to acquire x-ray attenuation projection data from different angles. By way of one non-limiting example, the detector array is able to acquire thirty projections, or views, per second, which provides substantially improved coverage, not to mention 3D coverage, over imaging systems integrated with the radiation therapy system 14.

The C-arm x-ray imaging system 200 also includes an operator workstation 222, which typically includes a display 224; one or more input devices 226, such as a keyboard and mouse; and a computer processor 228. The computer processor 228 may include a commercially available programmable machine running a commercially available operating system. The operator workstation 222 provides the operator interface that enables scanning control parameters to be entered into the C-arm x-ray imaging system 200. In general, the operator workstation 222 is in communication with a data store server 230 and an image reconstruction system 232. By way of example, the operator workstation 222, data store sever 230, and image reconstruction system 232 may be connected via a communication system 234, which may include any suitable network connection, whether wired, wireless, or a combination of both. As an example, the communication system 234 may include both proprietary or dedicated networks, as well as open networks, such as the internet. As will be described, the communications system 234 may also facilitate communication with the coordination system 158 that coordinates overall operation of the C-arm system 200 with the radiation therapy system 14/IGRT system 100.

The operator workstation 222 is also in communication with a control system 236 that provides local control of the C-arm x-ray imaging system 200. The control system 236 generally includes a C-axis controller 238, a pivot axis controller 240, an x-ray controller 242, a data acquisition system ("DAS") 244, and a table controller 246. The x-ray controller 242 provides power and timing signals to the x-ray source assembly 204, and the table controller 246 is operable to move the subject table 18 to different positions and orientations within the C-arm x-ray imaging system 200.

The rotation of the gantry 202, to which the x-ray source assembly 204 and the x-ray detector array assembly 206 are coupled, is controlled by the C-axis controller 238 and the pivot axis controller 240, which respectively control the rotation of the gantry 202 about the C-axis and the pivot axis 216. In response to motion commands from the operator workstation 222, the C-axis controller 238 and the pivot axis controller 240 provide power to motors in the C-arm x-ray imaging system 200 that produce the rotations about the C-axis and the pivot axis 216, respectively. For example, a program executed by the operator workstation 222 and overseen by the coordination system 158 generates motion commands to the C-axis controller 238 and pivot axis controller 240 to move the gantry 202, and thereby the x-ray source assembly 204 and x-ray detector array assembly 206, in a prescribed scan path. In some implementations, the coordination system 158 may directly control the control system 236, or various controllers/systems, therein to acquire imaging and determine or modify the prescribed scan path. The coordination system 158 may also receive various data, signals and information from the control system 236, such as positional information and imaging information.

The DAS 244 samples data from the one or more x-ray detectors in the x-ray detector array assembly 206 and converts the data to digital signals for subsequent processing. For instance, digitized x-ray data is communicated from the DAS 244 to the data store server 230. The image reconstruction system 232 then retrieves the x-ray data from the data store server 230 and reconstructs an image therefrom. In some implementations, the image reconstruction system 232 may be configured to reconstruct multi-dimensional images (e.g. 1D, 2D, 3D or 4D) in substantially real-time. To this end, image reconstruction system 230 may include a commercially available computer processor, or may be a highly parallel computer architecture, such as a system that includes multiple-core processors and massively parallel, high-density computing devices. Optionally, image reconstruction can also be performed on the processor 228 in the operator workstation 722. Reconstructed images can then be communicated back to the data store server 230 for storage or to the operator workstation 222 to be displayed to the operator or clinician. Furthermore, as will be described, reconstructed images may be communicated to and used by, for example, the coordination system 158, to control operation of the radiation therapy system 14/IGRT system 200 in substantially real-time.

The C-arm x-ray imaging system 200 may also include one or more networked workstations 248. By way of example, a networked workstation 248 may include a display 250 or touchscreen; one or more input devices 252, such as a keyboard, and a mouse; and a processor 254. The networked workstation 248 may be located within the same facility as the operator workstation 222, or in a different facility, such as a different healthcare institution or clinic.

The networked workstation 248, whether within the same facility or in a different facility as the operator workstation 222, may gain remote access to the data store server 230, the image reconstruction system 232, or both via the communication system 234. Accordingly, multiple networked workstations 248 may have access to the data store server 230, the image reconstruction system 232, or both. In this manner, x-ray data, reconstructed images, or other data may be exchanged between the data store server 230, the image reconstruction system 232, and the networked workstations 248, such that the data or images may be remotely processed by the networked workstation 248. This data may be exchanged in any suitable format, such as in accordance with the transmission control protocol ("TCP"), the Internet protocol ("IP"), or other known or suitable protocols.

Figure 4:
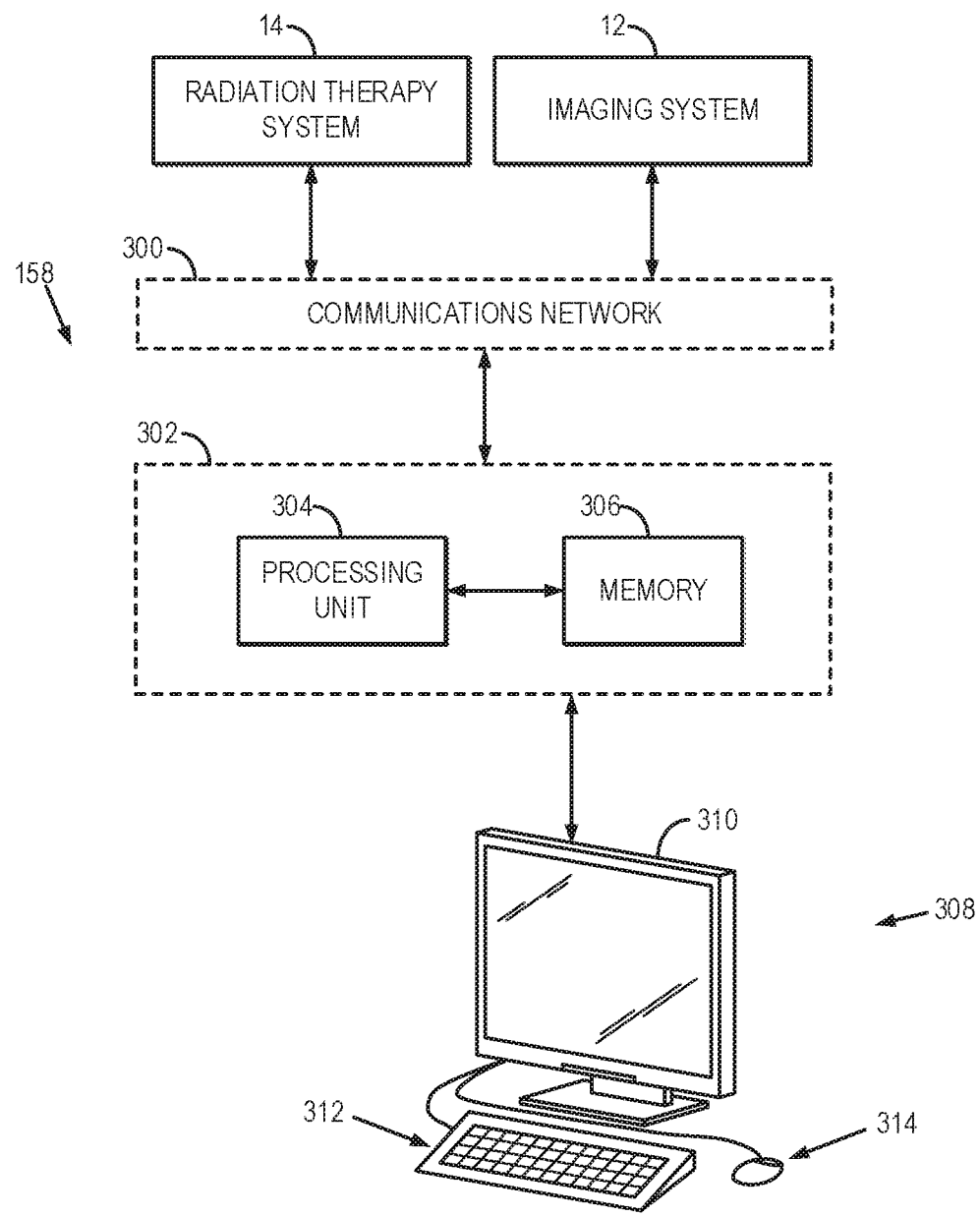
FIG. 4 is a block diagram of a control system for operating the system of FIG. 1.

Referring now to FIG. 4, the coordination system 158 will be described in greater detail. As described above, the coordination system 158 may be coupled through a communications network 300 to the radiation therapy system 14 and the imaging system 12 to coordinate control of the radiation therapy system 14 and the imaging system 12. The coordination system 158 may include one or more computer system 302 having at least one processing unit or processor 304 and a non-transitive memory or storage medium 306. The memory 306 may store instructions for operating the processor 304 as will be described. The computer 302 may include user interface components 308, such as a display 310 or touchscreen, keyboard 312, and mouse 314. In some non-limiting examples, the coordination system 158 may operate as a real-time radiation treatment delivery system.

In operation, the coordination system 158 may execute a variety of command and control operations or protocols to control and coordinate operation of the radiation therapy system 14 and the imaging system 12. To this end, the coordination system 158 may receive, process and transmit a variety of data, signals and information. In one example, the coordination system 158 may receive and process positional information, treatment information, or imaging information, and transmit instructions to operate the radiation therapy system 14 and/or imaging system 12 accordingly.

Figure 5:
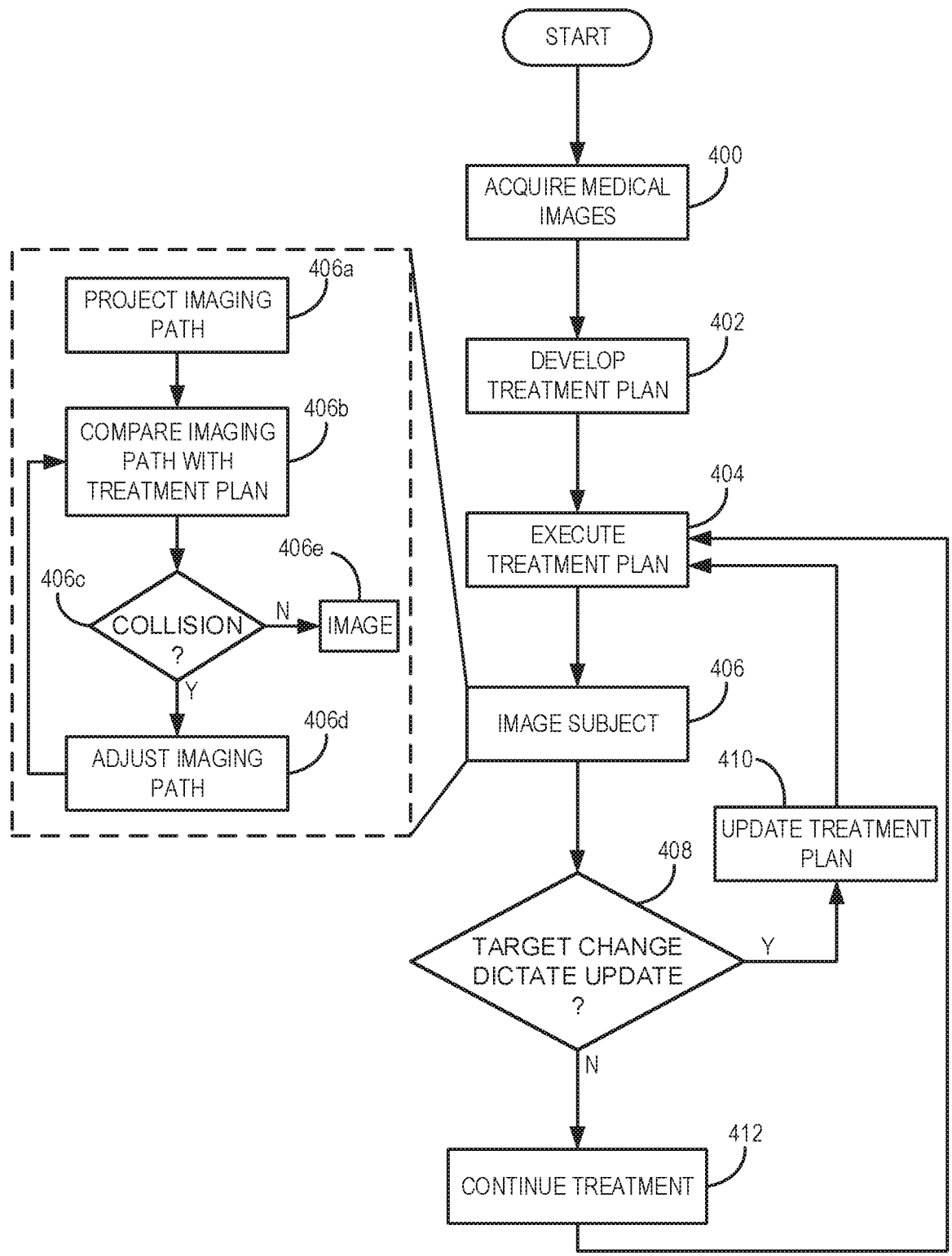
FIG. 5 is a flowchart setting forth non-limiting steps for operating the systems of FIGS. 1-4 in accordance with one aspect of the present disclosure.

Referring to FIG. 5, a flowchart setting forth steps of a process in accordance with aspects of the present disclosure is shown. Various steps of the process may be carried using one or more systems, as described with reference to FIGS. 1-4. In some implementations, steps of the process may be implemented as a program, firmware, or executable instructions hardwired or stored in non-transitory computer readable media.

The process may begin with acquiring medical images of the subject using an imaging system, as indicated by process block 400. This step may be carried out during a treatment planning phase by acquiring various multi-dimensional images (e.g. 1D, 2D, 3D, and 4D) including CT images, magnetic resonance (MR) images, positron emission tomography (PET) images, ultrasound (US) images, and other image types.

In some implementations, image acquisition at process block 400 may be performed using a system as described with reference to FIG. 1. To this end, the coordination system 158, may coordinate the operation of the imaging system 12 to acquire images at process block 400. When doing so, the coordination system 158 also controls the radiation therapy system 14 to avoid/not interfere with the acquisition of the medical imaging data by the imaging system 12. A treatment plan may then be developed at process block 402 using the acquired medical images. To do so, one of the above workstations may be used to create the plan, which may then then communicate the plan to the coordination system 158. Alternatively, or additionally, the treatment plan may be created of modified using the coordination system 158.

As an example, the treatment plan may be indicative of the various treatment fields or treatment beams to be delivered by the radiation therapy system 14, as well as a treatment path and timing for delivering the fields or beams. In some aspects, the treatment plan may also indicate the imaging path of the imaging system 12, where the imaging path is coordinated with the treatment path to avoid collision or interference between the imaging system 12 and the radiation therapy system 14. As used herein, imaging path may include previous, current and projected positions as well as orientations of the imaging system 12, and various components therein, relative to one or more coordinate systems. Similarly, the treatment path may include previous, current and projected positions as well as orientations of the radiation therapy system 14, and various components therein, relative to one or more coordinate systems. Such coordinate systems may include a coordinate system of the treatment room, a coordinate system of the subject, a coordinate system of the imaging system 12, a coordinate system of the radiation therapy system 14, and others.

In some implementations, process blocks 400 and 402 may be optional with respect to the process described herein. In this case, the treatment plan may be accessed or pushed from various workstations, databases or other data storage locations.

Based on an instruction from a clinician, a radiation therapy process may then begin at process block 404 by executing the treatment plan using a radiation therapy system. Prior to performing the treatment plan, a number of quality assurance steps may be carried out, including positioning the subject and adapting the treatment plan based on the current conditions of the subject. To do so, various images (e.g. 2D or 3D images) may be acquired to verify alignment, and any changes in the anatomy of the subject. To this end, the coordination system 158 may direct the imaging system 12 to acquire the images, and in so doing, coordinate operation of the radiation therapy system 14 and the imaging system 12 to avoid collisions or interference, as mentioned. The alignment (e.g. position and orientation) of the subject, as well as the treatment plan, may be adapted accordingly.

The radiation therapy process may also include imaging the subject, as indicated by process block 406. The images may be multi-dimensional (e.g., 2D or 3D) and used to monitor treatment or determine an effectiveness of the treatment. Additionally, the imaging may take place between or during the real-time delivery of the various treatment fields or beams in the treatment plan. To this end, process blocks 404 and 406 may be carried out sequentially, concurrently, or both.

In some aspects, the coordination system 158 may direct the imaging arm of the imaging system 12 to move around the subject to acquire either 2D radiograph images or 3D images, such as cone-beam CT images at process block 406. As shown in FIG. 5, the coordination system 158 projects an imaging path 406a that would be followed by the imaging system 12 to acquire desired images of a region of interest (e.g. treatment area or target area), and compares the imaging path to the treatment plan being used to control the radiation therapy system 14 at process block 406b. To this end, the coordination system 158 can determine whether a given imaging path followed at a given time will result in a collision or interference between the imaging system 12 and the radiation therapy system 14. Avoiding collision or interference may also take into account the subject, including the various movements that the subject may make. (e.g. periodic and non-periodic physiological movements, position shifts, and the like) If, at decision block 406c, a determination is made that there will be a collision or interference, the coordination system 158 updates or adjusts the imaging path to be followed by the imaging system 12 at process block 406d. If no collision is projected, the subject is imaged using the imaging path at process block 406e, which achieves the overall process reflected at process block 406.

When the images acquired at process block 404 are real-time images acquired during the performance of the treatment plan by the radiation therapy system 14, the coordination system 158 analyzes the images, in substantially real-time, and determines if the target area of the radiation therapy has appreciably changed at decision block 408. If so, the coordination system 158 can adapt or update the treatment plan at process block 410 to account for the changes revealed by the real-time images, for instance due to subject movement or target motion (e.g. translation, rotation, and distortion). The updated treatment plan may therefore compensate for the detected subject movement or target motion. In some aspects, updating the treatment plan may also accommodate effective therapy over various treatment sessions, and so on. If no changes are detected, the treatment is continued at process block 412 and the process may iterate. As described herein, real-time imaging may be understood by one of ordinary skill in the art to represent the acquisition of images over a period of time that is sufficient to capture the relevant activity being imaged. For example, when imaging regions of interest that include the heart or lungs, real-time imaging may be performed using a temporal resolution or frequency that is sufficient to identify the various phases or sub-phases of the cardiac cycle or the respiration cycle. Similarly, when monitoring or tracking target or non-target regions of interest, imaging The above-described, coordinated, dual-robot system can be used to implement highly-adaptive therapies. For example, the above-described system can be used to track a moving tumor, such as a lung tumor, and move the therapy arm along with the moving tumor. The above-described systems and methods can coordinate the movement of a therapy arm and an imaging arm for collision prevention and navigation. In certain implementations, the robotic arm imaging device is a cone beam CT ("CBCT") that can acquire CT images in less than 10 seconds, whereas a CBCT disposed on a conventional c-arm gantry system can take 1 minute to acquire an image. The image arm can also move around the therapy arm without interference and acquire projection and volumetric images from angles that are inaccessible to imaging systems that are integrated with the therapy system and the stereotactic imager on typical radiation therapy systems. The present systems allow continuous and uninterrupted imaging while non-coplanar beams are being delivered.

Figure 6:
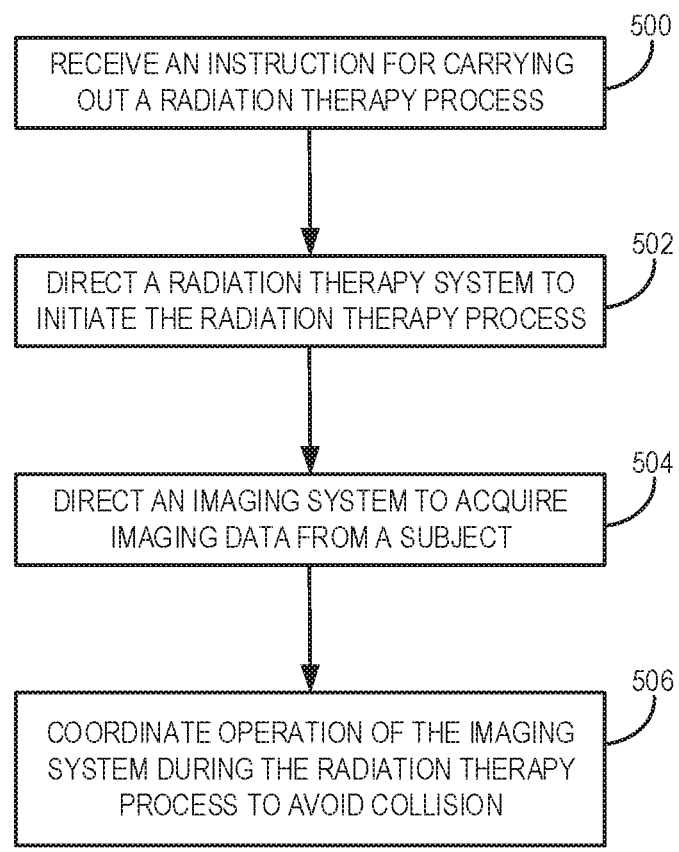
FIG. 6 is another flowchart setting forth non-limiting steps for operating the systems of FIGS. 1-4 in accordance with one aspect of the present disclosure.

Turning now to FIG. 6, another flowchart setting forth steps of a process in accordance with aspects of the present disclosure is shown. Various steps of process may be carried using one or more systems, as described with reference to FIGS. 1-4. In some realization, steps of the process may be implemented a program, firmware, or executable instructions hardwired or stored in non-transitory computer readable media.

The process may begin at process block 500 with receiving an instruction for carrying out radiation therapy process. The instruction may include selections provided by a user via an input device or element (e.g. a keyboard, a mouse, a touchscreen, so forth). In some aspects, the instruction may also include information corresponding to treatment plan (e.g. treatment fields, treatment path, and so on) pushed or obtained from a workstation, database, server, or other data storage location by way of one or more communication systems or networks.

Then, at process block 502, a radiation therapy process is initiated. In particular, based upon the instruction received, a coordination system may direct the radiation therapy system to begin executing the treatment plan and control a radiation source to direct radiation to one or more target areas in a subject (e.g. a tumor).

As indicated by process block 504, an imaging system may also be directed by the coordination system to acquire imaging data from the subject. For example, two-dimensional (2D) radiographic images or three-dimensional (3D) images, such as cone-beam CT images, may be acquired at process block 504, although other images may also be acquired (e.g. 1D or 4D images). In some aspects, imaging data may be acquired in substantially real-time. The imaging data may also be analyzed to determine whether a target area in the subject has changed. If so, the treatment plan may be updated, as described.

In some aspects, radiation therapy and imaging performed at process blocks 502 and 504 may be performed sequentially, as well as concurrently. As such, operation of the imaging system is coordinated during the radiation therapy process to avoid collision or interferences between the radiation therapy system and the imaging system, as indicated by process block 506. In some aspects, coordination takes place during movement of the radiation source about the subject. As described, this step may include projecting an imaging path of the imaging system and comparing the imaging path with a treatment path of the radiation therapy system. If a collision or interference is determined, the imaging path may be adjusted to avoid collision/interference. For example, the position and/or orientation of the imaging system, or various components therein, may be adjusted. In some aspects, imaging may also be temporarily interrupted or stopped.

In some aspects, a report may also be generated and provided by the coordination system. The report may be in any form and include any information, including images, projected imaging paths, treatment paths, treatment status, imaging status, and so on.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

What is claimed is:

1. A system for coordinating radiation therapy and imaging processes, the system comprising:
   a radiation therapy system comprising a radiation source mounted on a robotically-controlled system including an articulated arm, the robotically-controlled system being is configured to move the radiation source about a subject and direct radiation to a target area in the subject according to a treatment plan, wherein the articulated arm allows the radiation source to move with at least 4 degrees of freedom, and wherein the articulated arm is configured to move the radiation source in three dimensions;
   an imaging system configured to acquire imaging data from the subject, wherein the imaging system and the radiation therapy system are independently movable; and
   a coordination system configured to coordinate operation of the imaging system to acquire the imaging data from the subject during movement of the radiation source about the subject according to the treatment plan to avoid collision of the radiation therapy system with the imaging system.

2. The system of claim 1, wherein the imaging system comprises a robotically-controlled arm independent from the robotically-controlled system of the radiation therapy system;
   wherein the robotically-controlled system includes a first base that is configured to be supported by the ground, the articulated arm being coupled to the first base;
   wherein the imaging system includes a second base different from the first base, the second base being configured to be supported by the ground, the robotically-controlled arm being coupled to the second base.

3. The system of claim 1, wherein the imaging system is further configured to acquire three-dimensional (3D) imaging data, or four-dimensional (4D) imaging data, or a combination thereof.

4. The system of claim 1 wherein the imaging system comprises a cone beam computed tomography system.

5. The system of claim 1 wherein the robotically-controlled system is configured to allow the radiation source to move with at least 6 degrees of freedom.

6. The system of claim 1, wherein the coordination system is further configured to project an imaging path for imaging system and compare the imaging path with a treatment path corresponding to the treatment plan.

7. The system of claim 6, wherein the coordination system is further configured to adjust at least the imaging path based on the comparison.

8. The system of claim 1, wherein the coordination system is further configured to analyze the imaging data to determine a change in the target area.

9. The system of claim 8, wherein the coordination system is further configured to update the treatment plan based on the change.

10. A method for coordinating radiation therapy and imaging processes, the method comprising:
    receiving an instruction for carrying out a radiation therapy process corresponding to a treatment plan;
    directing, using a coordination system, a radiation therapy system to initiate the radiation therapy process in which a radiation source mounted on a robotically-controlled system directs radiation to a target area in a subject according to the treatment plan, wherein the robotically-controlled system includes an articulated arm and a radiation source coupled to the articulated arm, the articulated arm allowing the radiation source to move with at least 4 degrees of freedom;
    directing, using the coordination system, an imaging system to acquire imaging data from the subject, wherein the imaging system and the radiation therapy system are independently movable; and
    coordinating, using the coordination system, operation of the imaging system during movement of the radiation source about the subject to avoid collision of the radiation therapy system with the imaging system.

11. The method of claim 10, wherein the method further comprises directing the imaging system to acquire three-dimensional (3D) imaging data, or four-dimensional (4D) imaging data, or a combination thereof.

12. The method of claim 10, wherein the method further comprises:
    projecting an imaging path for imaging system;

comparing the imaging path with a treatment path corresponding to the treatment plan using the coordination system; and adjusting at least the imaging path based on the comparison.

13. The method of claim 10, wherein the method further comprises analyzing the imaging data to determine a change in the target area.

14. The method of claim 13, wherein the method further comprises updating the treatment plan based on the change.

15. The system of claim 1, wherein the coordination system is configured to direct an imaging arm of the imaging system to move around the subject to acquire the imaging data during movement of the radiation source.

16. The system of claim 1, wherein the imaging system includes an x-ray detector that is a portal image device.

17. A system for coordinating radiation therapy and imaging processes, the system comprising:

a radiation therapy system comprising a radiation source mounted on an articulated arm, the articulated arm configured to move the radiation source about a subject and direct radiation to a target area in the subject according to a treatment plan, the articulated arm being configured to allow the radiation source to move with at least 4 degrees of freedom, wherein the articulated arm is configured to move the radiation source in three dimensions;

a computed tomography (CT) imaging system including an x-ray detector that is pivotable about a first point and a second point, the CT imaging system being configured to acquire CT imaging data from the subject, and wherein the CT imaging system and the radiation therapy system are independently movable, and wherein the CT imaging system includes a robotically-controlled arm that is configured to move the x-ray detector in three dimensions; and a coordination system including a processor, the coordination system being configured to coordinate operation of the CT imaging system to acquire the CT imaging data from the subject during movement of the radiation source about the subject according to the treatment plan to avoid collision of the radiation therapy system with the CT imaging system.

18. The system of claim 17, wherein the CT imaging system is a cone beam computed tomography system; and wherein the CT imaging system comprises a gantry that is configured to pivot about three points.

19. The system of claim 17, wherein the CT imaging data is at least one of three-dimensional (3D) imaging data, or four-dimensional (4D) imaging data.

20. The system of claim 19, wherein the coordination system is configured to:

determine a collision between a projected imaging path with a treatment path of the radiation therapy system;

adjust the projected imaging path to avoid collision between the CT imaging system and the radiation therapy system, based on the determined collision.

\* \* \* \* \*